(12) United States Patent
Wang et al.

(10) Patent No.: US 9,067,985 B2
(45) Date of Patent: Jun. 30, 2015

(54) BACTERIORHODOPSIN FUSION MEMBRANE PROTEIN EXPRESSION SYSTEM

(71) Applicant: Academia Sinica, Taipei (TW)

(72) Inventors: Andrew H.-J. Wang, Taipei (TW); Min-Feng Hsu, New Taipei (TW); Chii-Shen Yang, Taipei (TW); Hsu-Yuang Fu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/041,493

(22) Filed: Sep. 30, 2013

(65) Prior Publication Data

US 2014/0099667 A1    Apr. 10, 2014

Related U.S. Application Data

(60) Provisional application No. 61/710,681, filed on Oct. 6, 2012.

(51) Int. Cl.
*C07K 14/215* (2006.01)

(52) U.S. Cl.
CPC ........... *C07K 14/215* (2013.01); *C07K 2319/00* (2013.01); *C07K 2319/21* (2013.01); *C07K 2319/50* (2013.01)

(58) Field of Classification Search
None
See application file for complete search history.

(56) References Cited

U.S. PATENT DOCUMENTS

| 6,010,885 A * | 1/2000 | Turner et al. ................. 435/69.7 |
| 6,465,216 B2 | 10/2002 | Laible et al. |
| 2006/0211087 A1* | 9/2006 | Roosild et al. ............... 435/69.1 |

OTHER PUBLICATIONS

Turner G.J., Miereke L.J., Mitra A. K., Stroud R. M. , Betlach M. C., Winter-Vann A. (1999) Expression, purification, and structural characterization, of the bacteriorhodopsin-aspartyl transcarbamylase fusion protein. Protein Expr Purif., Nov.;17(2):324-38.
Shand R.F., Miereke L.J., Mitra A.K., Fong S.K., Stroud R.M., Betlach M.C. (1991) Wild-type and mutant bacterioopsins D85N, D96N, and R82Q: high-level expression in *Escherichia coli* Biochemistry. Mar. 26;30(12):3082-8.
Hsu M-F. Yu T-F, Chou C-C, Fu H-Y, Yang C-S, et al. (2013) Using *Haloarcula marismortui* Bacteriorhodopsin as a Fusion Tag for Enhancing and Visible Expression of Integral Membrane Proteins in *Escherichia coli*. PLoS ONE 8(2): e56363. doi.10.1371/journal.pone.0056363.
Hsu-Yuan Fu,Yu-Cheng Lin, Yung-Ning Chang, Hsiaochu Tseng, Ching-Che Huang, Kang-Cheng Liu,Ching-Shin Huang, Che-Wei Su, Rueyhung Roc Weng, Yin-Yu Lee, Wailap Victor Ng,and Chii-Shen Yang. A Novel Six-Rhodopsin System in a Single Archaeon. Journal of Bacteriology, Nov. 2010, p. 5866-5873.

* cited by examiner

*Primary Examiner* — Anne Gussow
*Assistant Examiner* — Addison D Ault
(74) *Attorney, Agent, or Firm* — Hsiu-Ming Saunders; Intellectual Property Connections, Inc.

(57) ABSTRACT

An expression vector is disclosed, which comprises: a) a polynucleotide sequence encoding a bacteriorhodopsin or a mutant bacteriorhodopsin; b) a multiple cloning site; c) a T7 promoter, d) a polyhistidine tag; e) a first protease cleavage site; f) optionally a second protease cleavage site; and g) optionally a linker; wherein the mutant bacteriorhodopsin comprises the residue corresponding to Asn94 of SEQ ID NO: 1. Also disclosed is a fusion membrane protein expression system, which comprises: a) a polynucleotide sequence encoding a mutant *Haloarcula marismortui* bacteriorhodopsin/D94N (HmBRI/D94N) or a *Haloquadratum walsbyi* bacteriorhodopsin (HwBR); b) a target membrane protein; and c) a T7 promoter, operably linked to the mutant HmBRI/D94N or HwBR and the target membrane protein. Host cells comprising the expression vector or the fusion membrane protein expression system and methods of using the same are also disclosed.

10 Claims, 6 Drawing Sheets

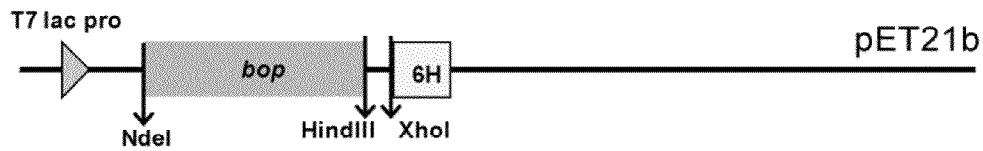
FIG. 2A
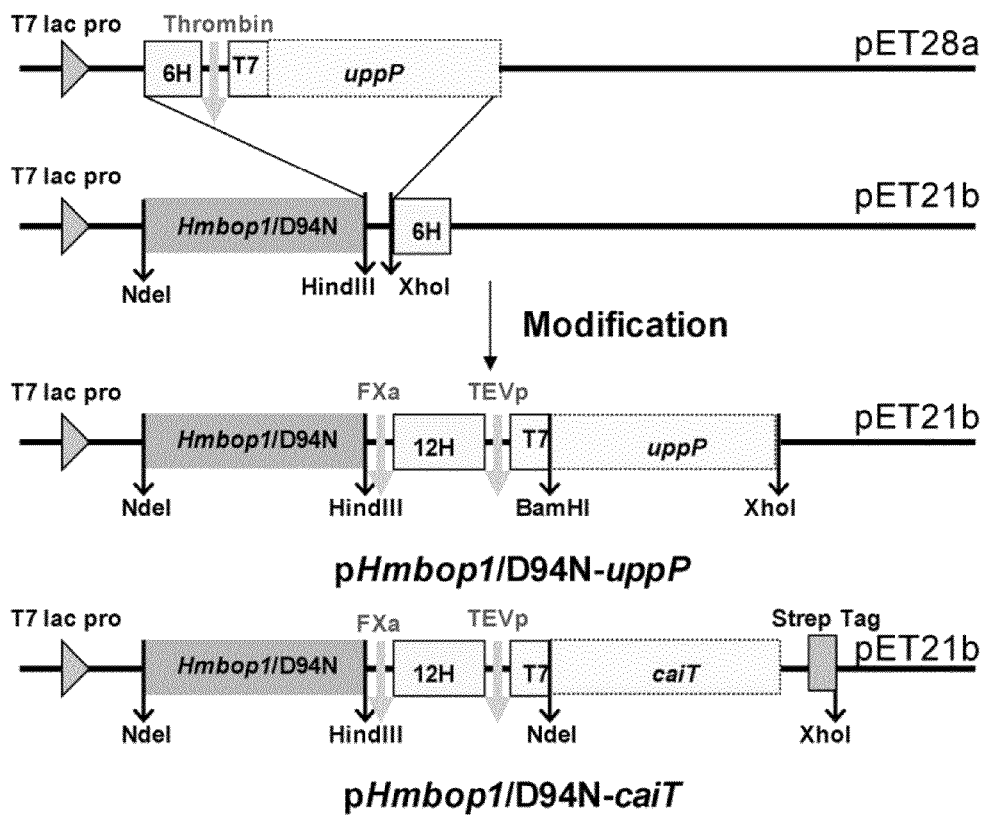
FIG. 2B
FIG. 3A
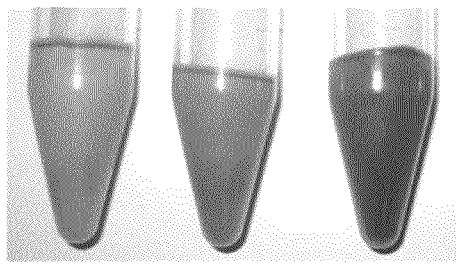
FIG. 3B
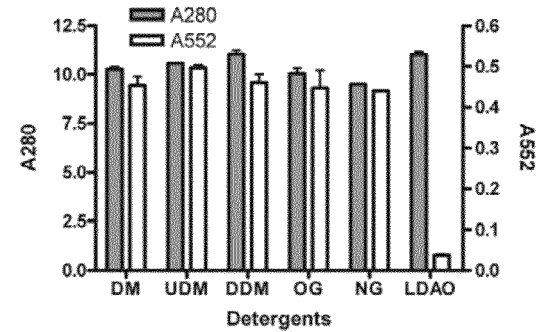

I. Fusion membrane protein expression
II. Membrane preparation
III. Detergent extraction
IV. 1st IMAC purification
V. TEVp cleavage
VI. 2nd IMAC purification
VII. SEC
VIII. Crystallization

BACTERIORHODOPSIN FUSION MEMBRANE PROTEIN EXPRESSION SYSTEM

REFERENCE TO RELATED APPLICATION

The present application claims the priority to U.S. Provisional Application Ser. No. 61/710,681, filed Oct. 6, 2012, which is herein incorporated by reference in its entirety.

FIELD OF THE INVENTION

The invention relates to the field of membrane protein, and more specifically to a membrane protein expression system.

BACKGROUND OF THE INVENTION

Integral membrane proteins constitute an important class of proteins with which are often involved in diverse biological functions, including G-protein coupled receptors (GPCRs), channels, transporters and enzymes. Approximately 20-35% of the open reading frames (ORFs) in the human genome are predicted to encode membrane proteins. Membrane proteins account for more than 50% of current drug targets. Structural information about these pharmaceutically useful membrane proteins will assist in the design of better drug molecules. However, despite the need for identifying membrane protein. structures, there are significantly fewer structures available for membrane proteins than for soluble proteins. Some of the major hurdles associated with membrane protein purification include the production of insufficient yields and the inability to obtain diffraction quality crystals.

SUMMARY OF THE INVENTION

In one aspect, the invention relates to an expression vector, which comprises:

a) a polynucleotide sequence encoding a bacteriorhodopsin or a mutant bacteriorhodopsin, wherein the bacteriorhodopsin and the mutant bacteriorhodopsin are at least 80% identical to the sequence selected from the group consisting of SEQ ID NOs: 3 and 1, respectively;

b) a multiple cloning site, located downstream from the C-terminus of the bacteriorhodopsin or the mutant bacteriorhodopsin;

c) a T7 promoter, operably linked to the bacteriorhodopsin or the mutant bacteriorhodopsin and the multiple cloning site;

d) a polyhistidine tag, located downstream from the C-terminus of the bacteriorhodopsin or the mutant bacteriorhodopsin and upstream from the N-terminus of the multiple cloning site;

e) a first protease cleavage site, located downstream from the C-terminus of the polyhistidine tag and upstream from the N-terminus of the multiple cloning site;

f) optionally a second protease cleavage site, located between the bacteriorhodopsin or the mutant bacteriorhodopsin and the polyhistidine tag, and g) optionally a linker located between the first protease cleavage site and the multiple cloning site;

wherein the mutant bacteriorhodopsin comprises the residue corresponding to Asn94 of SEQ ID NO: 1.

In one embodiment of the invention, the bacteriorhodopsin and the mutant bacteriorhodopsin are at least 90% identical to the sequence selected from the group consisting of SEQ ID NOs: 3 and 1, respectively.

In another embodiment of the invention, the amino acid sequence of the bacteriorhodopsin is SEQ ID NO: 3.

In another embodiment of the invention, the amino acid sequence of the mutant bacteriorhodopsin is SEQ ID NO: 1.

In another embodiment of the invention, the multiple cloning site comprises BamHI and XhoI restriction enzyme sites.

In another embodiment of the invention, the expression vector further comprises a target membrane protein located within the multiple cloning site.

In another embodiment of the invention, the target membrane protein is an integral membrane protein.

Further in another aspect, the invention relates to a host cell comprising the aforementioned expression vector.

In another embodiment of the invention, the host cell expresses a fusion protein comprising the bacteriorhodopsin or the mutant bacteriorhodopsin and the target membrane protein, wherein the N-terminus of the target membrane protein is located in the cytoplasm, and the host cell exhibits a purple color.

Further in another aspect, the invention relates to a fusion membrane protein expression system comprises: a) a polynucleotide sequence encoding a mutant *Haloarcula marismortui* bacteriorhodopsin/D94N (HmBRI/D94N) or a *Haloquadratum walsbyi* bacteriorhodopsin (HwBR); b) a target membrane protein, located downstream from the 3'-end of the HmBRI/D94N or HwBR; and c) a T7 promoter, operably linked to the mutant HmBRI/D94N or HwBR and the target membrane protein.

In one embodiment of the invention, the fusion membrane protein expression system further comprises:

d) a polyhistidine tag, located between the mutant HmBRI/D94N or HwBR and the target membrane protein;

e) a first protease cleavage site, located between the polyhistidine tag and the target membrane protein;

f) optionally a second protease cleavage site, located between the mutant HmBRI/94N or HwBR and the polyhistidine tag; and g) optionally a linker located between the first protease cleavage site and the target membrane protein.

In another embodiment of the invention, the first protease cleavage site is a Tobacco Etch Virus protease cleavage site, and the second protease cleavage site is a factor Xa cleavage site.

In another embodiment of the invention, the polyhistidine tag encodes more than 6 histidine residues.

In another embodiment of the invention, the aforementioned fusion membrane protein expression system exhibits an enhanced ability in expressing the target membrane protein for at least 15 folds as compared to a control expression system without the mutant HmBRI/D94N or HwBR.

Further in another aspect, the invention relates to a method for expressing a target membrane protein, which comprises inducing the aforementioned fusion membrane protein expression system to simultaneously express and fold a fusion protein within the cell membrane of an *E. coli* cell, wherein the fusion protein comprises the mutant *Haloarcula marismortui* bacteriorhodopsin/D94N (HmBRI/D94N) or the *Haloquadratum walsbyi* bacteriorhodopsin (HwBR) and the target protein.

In one embodiment of the invention, the inducing step comprises the step of adding retinal to fold the fusion protein within the cell membrane of the *E. coli* cell.

Yet in another aspect, the invention relates to a method of preparing a target membrane protein, which comprises:

a) generating an expression plasmid comprising a fusion protein by inserting a DNA encoding the target membrane protein into the multiple cloning site of the expression vector as aforementioned, wherein the fusion protein comprises the bacteriorhodopsin or a mutant bacteriorhodopsin and the target membrane protein;

b) transforming a host cell with the expression plasmid;

c) growing the transformed host cell for a period of time to obtain a population of the transformed host cells;

d) inducing the transformed host cells to express the fusion protein;

e) harvesting and then disrupting the host cells expressing the fusion protein;

f) collecting the fusion protein by ultracentrifugation;

g) extracting the fusion protein with a detergent;

h) purifying the fusion protein with a first affinity column;

i) eluting the fusion protein from the first affinity column;

j) digesting the fusion protein with a first protease to free the target membrane protein;

k) removing uncleaved fusion protein, His-tagged bacteriorhodopsin and the first protease with a second affinity column; and l) collecting the target membrane protein in a flow-through from the second affinity column.

In one embodiment of the invention, the aforementioned method further comprises: m) subjecting the collected target membrane protein to a size exclusion column; and n) eluting the target membrane protein from the size exclusion column.

In another embodiment of the invention, the first protease in the aforementioned digesting and removing steps is a His-tagged TEV protease. The host cell may be an *E. coli* cell.

Further in another embodiment of the invention, the aforementioned method further comprises the step of crystalizing the target membrane protein.

Yet in another embodiment of the invention, the detergent does not comprise lauryldimethylamine-N-oxide.

These and other aspects will become apparent from the following description of the preferred embodiment taken in conjunction with the following drawings, although variations and modifications therein may be affected without departing from the spirit and scope of the novel concepts of the disclosure The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 2 is a schematic illustration of the cloning strategy for the pHmbop1/D94N-uppP systems. (A) All the bop genes were constructed into pET21b with C terminal (His)$_6$ tag. (B) The target gene, *E. coli* uppP gene was constructed into pET28a with 6×His tag, thrombin cleavage site and T7 tag at 5' end. Hmbop1/D94N (bop1 is the gene of BRI) was constructed in pET21b with a 3' end-6×His tag. The 6×His-thrombin cleavage site-T7 tag-uppP fragment constructed in pET28a was then subcloned into the 3' end of Hmbop1/D94N. After several modifications, pHmbop1/D94N-uppP was generated for fusion protein expression. For construction of pHmbop1/D94N-caiT, a Strep tag was inserted at the 3' end of the caiT gene.

FIG. 3 shows: (A) Expressed *E. coli* cell pellets. Expressed cell pellets induced by IPTG and retinal of *E. coli* C43(DE3) transformed with pET21b, HmBRI and D94N. (B) Detergent screening of HmBRI/D94N. Various common detergents including DM, UDM, DDM, OG, NG and LDAO were tested. Gray bars represent the total protein ($A_{280}$) of detergent extracted membrane fractions and the open bars represent the specific absorption of HmBRI/D94N ($A_{552}$) of detergent extracted membrane fractions.

DETAILED DESCRIPTION OF THE INVENTION

Figure 1A:
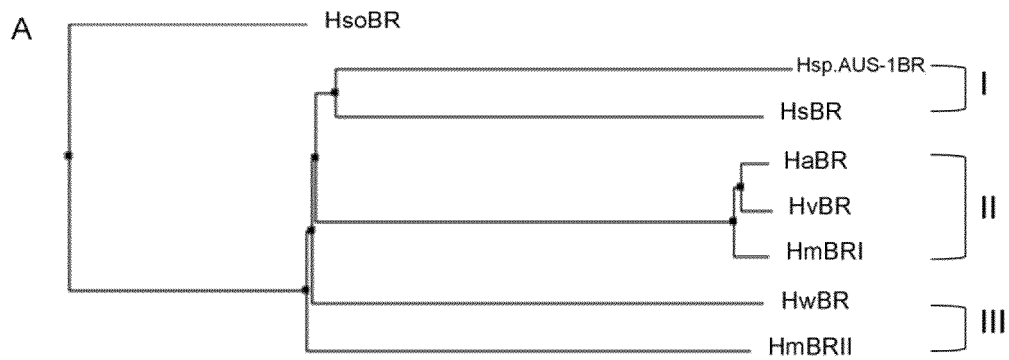
FIG. 1 shows a phylogenic tree and multiple sequence alignment of bacteriorhodopsins. (A) Phylogenic tree of haloarchaeal bacteriorhodopsins. (B) HsBR (PDB code: 1C3W; SEQ ID NO: 4), HmBRI (SEQ ID NO: 5), HmBRII (SEQ ID NO: 2) and HwBR (SEQ ID NO: 3) are aligned using ClustalW (Thompson et al. (1994) CLUSTAL W: "Improving the sensitivity of progressive multiple sequence alignment through sequence weighting, position-specific gap penalties and weight, matrix choice" Nucleic Acids Res 22: 4673-4680). The seven-transmembrane helices are labeled A to G. The proton acceptor residues (Asp) are labeled with circles. The position of HmBRI/D94N is labeled with a triangle, and the residue Lys bound to retinal by Schiff base interaction is labeled with a star.

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

A multiple cloning site (MCS), also called a polylinker, is a short segment of DNA which contains many (up to ~20) restriction sites. Restriction sites within an MCS are typically unique, occurring only once within a given plasmid.

An integral membrane protein (IMP) is a protein molecule (or assembly of proteins) that is permanently attached to the biological membrane. Proteins that cross the membrane are surrounded by "annular" lipids. Such proteins can be separated from the biological membranes only using detergents, nonpolar solvents, or sometimes denaturing agents.

DM (n-decyl-β-D-maltoside), UDW (n-undecyl-β-D-Maltoside), DDM (n-dodecyl-β-D-maltoside), OG (n-octyl-β-D-glucoside), NG (n-nonyl-β-D-glucoside) and LDAO (lauryldimethylamine-N-oxide).

The SEQ ID NOs. of mutant bacteriorhodopsin and wild-type bacteirorhodopsins are as follows: HmBRI/D94N (SEQ ID NO: 1) is a mutant of HmBRI at Asp94; HmBRII (SEQ ID NO: 2); HwBR (SEQ ID NO: 3); HsBR (SEQ ID NO: 4); HmBRI (SEQ ID NO: 5).

A Factor Xa cleavage site is IEGR (the cleavage is after R); TEV protease cleavage site is ENLYFQG (the cleavage site is between Q and G).

A linker is a short peptide sequence that occur between protein domains. Linkers are often composed of flexible residues like glycine and serine so that the adjacent protein domains are free to move relative to one another. Longer linkers are used when it is necessary to ensure that two adjacent domains do not sterically interfere with one another.

The terms "T7 tag" and "T7 epitope tag" are interchangeable. T7 tag is about 11-16 amino acids, being derived from the T7 gene 10 which is the naturally most abundant phage T7 gene product. For example, NOVAGEN™ T7●TAG®.

Bacteriorhodopsins from photoreceptive archaebacteria, often found in hypersaline environments (3-5 M NaCl) such as salt lakes, salt ponds, and marine salterns are among the best-studied integral membrane proteins. Thus far, the complete genome of four such species has been sequenced: *Halobacterium salinarum* (Ng et al. (2000) *Proc Natl Acad Sci USA* 97: 12176-12181), *Haloarcula marismortui* (Baliga et al. (2004) *Genome Res* 14: 2221-2234), *Haloquadratum walsbyi* (Bolhuis H, Palm P. Wende A, Falb M, Rampp M, et al. (2006) *BMC Genomics* 7: 169), and the haloalkaliphile *Natronomonas pharaonis* (Falb et. al. (2005) *Genome Res* 15: 1336-1343). From genomic analysis, it can be seen that their metabolism is considerably different from each other based on their acidic protein machineries, respiratory chains and rhodopsins. In *H. salinarum*, the sole bacteriorhodopsin protein (HsBR) occupies nearly 75% of the cell surface area, forming a hexagonally symmetric purple membrane composed of three identical protomers. The HsBR structure has been determined at high resolution by x-ray diffraction, which revealed seven transmembrane α-helices and one bound retinal molecule covalently linked to Lys216 forming the Schiff base. After absorbing a photon, the retinal is isomerized from the all-trans to the 13-cisconfiguration. To investigate the photocycle of HsBR, site-directed mutagenesis of aspartate residues at positions 85, 96, and 212 demonstrated that these mutants reduced the proton pumping activity. A sp96 serves as the internal proton donor in the reprotonation of the Schiff base, and the D96N mutation increases the M state decay rate (Otto et al. (1989) *Proc Natl Acad Sci USA* 86: 9228-9232).

The relatively well-established experimental protocols associated with HsBR allow us to consider other BRs for structural analysis as well as their possible use as protein carriers. Recently, Yang and his colleagues have cloned and expressed six putative photoreceptor proteins from *H. marismortui* in *E. coli* C43(DE3) (Fu et al (2010) *J Bacteriol* 192: 5866-5873). The D94N mutant which has a longer M state lifetime was generated for the analysis of the specific photocycle of HmBRI. Surprisingly, HmBRI/D94N could be overexpressed in *E. coli* (40-70 mg/L culture). We designed systems in which the target membrane protein was fused with HmBRI/D94N incorporating a histidine purification tag (His-tag) plus a Tobacco Etch Virus protease (TEVp) cleavage site at the N terminus of target protein. The undecaprenyl pyrophosphate phosphatase (UppP) and carnitine transporter (CaiT) of *E. coli* were chosen as the target membrane proteins to demonstrate the utility of our design. We have successfully purified milligram quantities (per liter of *E. coli* culture) of active UppP and CaiT integral membrane proteins, as judged by SDS-PAGE, matrix-assisted laser desorption/ionization mass spectrometry (MALDI-MS), functional assays and crystallization studies. Therefore the structurally robust and biochemically stable HmBRI/D94N is a suitable fusion membrane protein fusion tag for the large-scale preparation of integral membrane proteins. With further modification of our system, new platforms can be tailored for high-throughput analysis, e.g., by incorporating parallel cloning vectors that use additional fusion tags (Hsu M-F, Yu T-F, Chou C-C, Fu H-Y, Yang C-S, et al. (2013) "Using *Haloarcula marismortui* Bacteriorhodopsin as a Fusion Tag for Enhancing and Visible Expression of Integral Membrane Proteins in *Escherichia coli*" PLoS ONE 8(2): e56363, which is incorporated herein by reference in its entirety). The invention is related to a high-level expression system of integral membrane proteins in *Escherichia coli* by using a mutated bacteriorhodopsin (BR) from, e.g., *Haloarcula marismortui* (such as HmBRI/D94N) as a fusion partner. A purification strategy was designed by incorporating a His-tag on the target membrane protein for affinity purification and an appropriate protease cleavage sites to generate the final products. The fusion system can be used to detect the intended target membrane proteins during overexpression and purification either with the naked eye or by directly monitoring their characteristic optical absorption. This approach was applied to produce functional integral membrane proteins. This technology could facilitate the development of a high-throughput strategy to screen for conditions that improve the yield of correctly folded target membrane proteins, while enabling other robust BRs to be incorporated in this system.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
Construction of Expression Plasmids

The plasmid vector pHmbop1/D94N (the bop1 is the gene encodes BRI) was constructed previously (Fu et al. (2010) "A novel six-rhodopsin system in a single archaeon" *J Bacteriol* 192; 5866-5873, which is incorporated herein by reference), and the Hwbop1 was constructed as well (FIG. 2A). The *E. coli* uppP gene was PCR-amplified from *E. coli* BL21(DE3) chromosome. BamHI and XhoI restriction sites were introduced at the 5' and 3' ends, respectively. The gene was then inserted into the pET28a vector (NOVAGEN). The vector for overexpression of the HmBRI/D94N-UppP fusion protein was constructed as follows. The 6×His-thrombin cleavage site-T7 tag-uppP fragment from pET28a was subcloned into the 3' end of Hmbop1/D94N in pET21b. Furthermore, several modifications were used to generate an efficient expression vector, pHmbop1/D94N-uppP, including the exchange of a thrombin cleavage site for a Factor Xa site (IEGR↓), extension of the 6×His tag to a 12×His tag and insertion of TEV protease cleavage site (ENLYFQ↓G) to the 5'end of T7 tag (i.e., internal T7 epitope tag, abbreviated as T7 in FIG. 2B). Based on the resultant plasmid, the genes encoding the target proteins could be inserted between BamHI and XhoI sites (FIG. 2B). For construction of caiT, a Strep tag was inserted at the 3' end followed by caiT gene to assist in additional purification steps.

Protein Expression and Purification

The expression vectors harboring the Hmbop1/D94N, Hwbop1, Hmbop1/D94N-uppP and -caiT genes were transformed into *E. coli* C43(DE3) which were grown at 37° C. in LB medium containing 100 μg/ml ampicillin. When the optical density of the culture reached an $OD_{600}$ of 1.0, the protein expression was induced for 5 hrs by the addition of 0.5 mM isopropyl-β-D-thiogalactoside (IPTG) and 5-10 mM all-trans retinal (Sigma) at 37° C. For purification of HmBRI/D94N and HwBR, we directly treated the disrupted cell lysate in 50° C. water bath for 30 mins. The pellet with the membrane fraction was obtained by centrifugation at 20,000 rpm for 30 mins. After extracting the protein from membrane fraction using buffer A (50 mM Tris, pH 7.5, 150 mM NaCl) with 2% DM overnight, we purified the protein by Ni-NTA column and eluted by buffer A containing 500 mM imidazole and 0.2% DM. The purified protein was finally dialyzed against 50 mM MES, pH 6.5, 150 mM NaCl and 0.2% DM.

For the purification of UppP and CaiT, the cells were harvested and re-suspended in buffer A. The cells were disrupted by Constant Cell Disruption Systems (Constant Systems Ltd), and the membrane and soluble proteins were separated by ultracentrifugation at 100,000×g for 1.5 h. The resulting pellet was solubilized by incubation in buffer A supplemented with 20 mM imidazole and 1% (w/v) DDM detergent overnight at 4° C. The latter solution was centrifuged (35,000 rpm for 1 hr at 4° C. in a Beckman Ti45 rotor), and the supernatant was loaded onto Ni-NTA column and washed with buffer A containing 20 mM imidazole and 0.05% DDM. TEV protease digestion was performed after exchanging the buffer into buffer A, and the reaction mixture was incubated at 4° C. overnight.

The native UppP was eluted by washing with buffer A containing 0.05% DDM. Size exclusion chromatography (SEC) was performed using a SUPERDEX™ 200 HR 10/30 column (GE Healthcare) equilibrated with two column volumes of buffer A with 0.05% DDM. Elution of the proteins was followed at 280 nm. A 500 μl aliquot of the protein sample was loaded onto the column at a flow rate of 0.3 ml/min.

For CaiT purification, a STREP-TAG™ (GE Healthcare) purification step was further introduced and performed prior to the SEC step.

Detergent Screening

Commonly used detergents-DM, UDM, DDM, OG, NG and LDAO- were prepared in buffer A at concentrations of 1~2%. The expressed HmBRI/D94N *E. coli* cells were disrupted by Constant Cell Disruption Systems (Constant Systems Ltd). One milliliter aliquots of the suspension were transferred into 1.5 ml tubes and incubated at 50° C. for 30 mins. The membranes containing the purple HmBRI/D94N were harvested and centrifuged for 10 mins at 13,000 rpm. The detergent solutions (1 ml each) were added into the tubes and incubated at 4° C. for at least 1 hr to solubilize the membranes. The solutions were centrifuged at 13,000 rpm for 10 mins to discard the insoluble components. The supernatants were analyzed by UV-VIS spectroscopy at 280 nm and 552 nm using Nanodrop 1000 spectrophotometer (Thermo). All detergent tests were performed in triplicate.

Protein Monitoring

Electrophoresis was carried out in SDS-PAGE using a NUPAGE electrophoresis system (INVITROGEN™) and conditions were prepared for membrane proteins. Protein concentration was quantified by UV-VIS spectroscopy at 280 nm and 552 nm using Nanodrop 1000 spectrophotometer (Thermo).

Phosphatase Assay

UppP activity was determined by the Malachite Green assay using Phosphate Colorimetric Assay Kit purchased from BioVision. The enzymatic assay reaction mixture (200 µl) containing 50 mM Tris-HCl, pH 7.5, 150 mM NaCl, 0.2% DDM, 100 µM substrate (Fpp) and appropriately diluted purified UppP was incubated at 37° C. The reaction was quenched by adding 30 µl of Malachite Green Reagent and then the tubes were incubated for 30 min at room temperature. After incubation, the reaction mixture was transferred to 96-well plates and the released phosphate that reacted with Malachite Green was measured at 650 nm according to the reaction time course. The amounts of released phosphate were quantified relative to a phosphate standard curve.

CaiT Activity Assay

The CaiT activity assay was modified from the method described previously. The fluorescence intensity measured at 339.50 nm was used to calculate the apparent affinity constant, $K_{0.5}$, which reflects the ligand concentration, causing a half-maximum change in CaiT fluorescence.

Crystallization and X-ray Diffraction Data Collection

The HmBRI/D94N crystals were grown at 20° C. using sitting drop vapor diffusion method. The protein (~3 mg/ml) was mixed 1:1 with a reservoir solution composed of 50 mM HEPES, pH 7.8 and 26% (v/v) PEG600. The X-ray diffraction datasets were collected at BL44XU, Spring-8, Japan and processed using HKL2000. The HwBR crystals were grown at 20° C. using sitting drop vapor diffusion method. The protein (~10 mg/ml) was mixed 1:1 with a reservoir solution composed of 0.1 M Tris-HCl, pH 8.0, 0.2 M calcium chloride and 44% (v/v) PEG400.

Native CaiT crystals were grown using the sitting-drop vapor-diffusion method at 20° C. by mixing an equal volume of 5.7 mg/ml of the protein with a reservoir solution composed of 50 mM magnesium acetate, pH 4.5, 26%-28% (v/v) PEG 400, and 50-200 mM NaCl. X-ray diffraction datasets were collected on a ADSC Quantum315 CCD-detector at the BL13B beamline at the National Synchrotron Radiation Research Center (NSRRC), HsinChu, Taiwan. The phases were obtained by molecular replacement using *E. coli* CaiT complexed with γ-butyrobetaine as a template (2WSX). PHENIX and COOT programs are used for molecular replacement and structure viewer.

Results

Selection of Bacteriorhodopsin

Figure 1B:
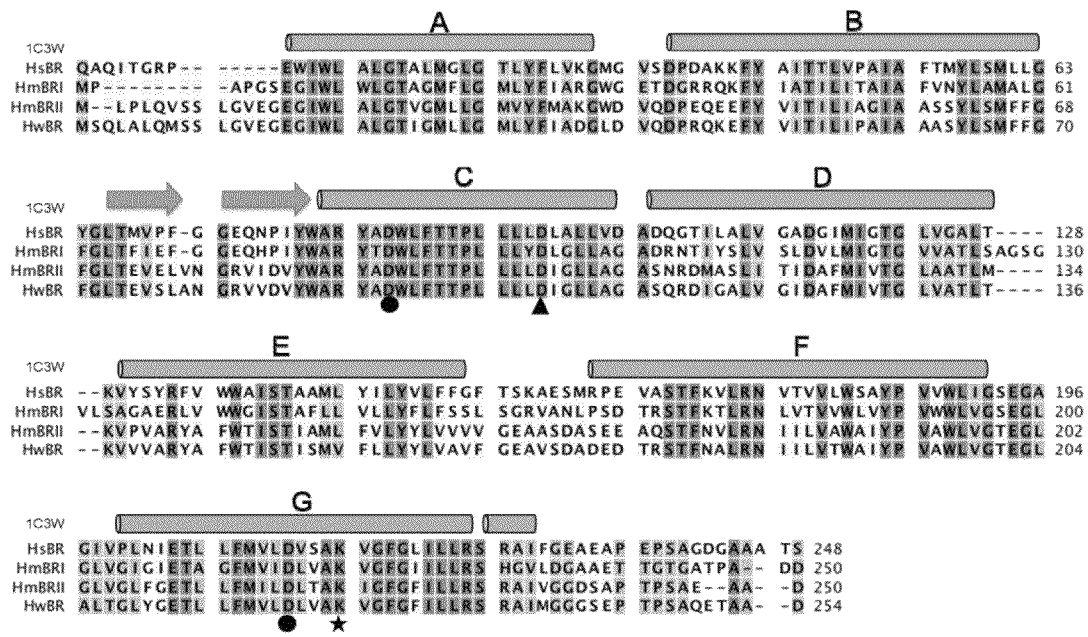

Haloarchaeal bacteriorhodopsins (BRs) are well-known purple integral membrane proteins. Furthermore, BR is stable above 80° C. and under pH conditions ranging from 1.0 to 12.0 in an aqueous environment. The retinal chromophore is bound tightly to the Lys in the pocket. There are several BRs divided into three groups (FIG. 1A), even though they have similar sequences (FIG. 1B). We chose to study the protein expression of HsBR, HmBRI and HwBR in *E. coli* and characterize their biophysical properties. In this study, BRs were cloned into pET21b with a 3' end-6×His tag and were overexpressed in *E. coli* C43(DE3) (FIG. 2A). HsBR is the best-studied BR with low expression levels in the membrane fraction with *E. coli* as the host. In addition, the structures of HsBR and its mutants purified from the native source have been solved (Pebay-Peyroula et al. (1997) *Science* 277: 1676-1681; Luecke et al. (1999) *Science* 286: 255-261).

BR, a seven-transmembrane, purple integral membrane protein that is covalently bound to retinal through a Lys residue in helix G by the Schiff base action. The residues of BRs that are important for proton transfer are conserved, i.e., Asp85, 96, and 212 of HsBR (FIG. 1B). Fu et al (2010) (J Bacteriol 192: 5866-5873) successfully expressed six photorhodopsins from *Haloarcula marismortui* with high expression levels using pET21b as the expression vector and *E. coli* C43(DE3) as the host, and analyzed their functions. The D94N mutation of HmBRI was generated for trapping the photocycle in the M state and slowing the rate of photocycle. When HmBRI/D94N was expressed with all-trans retinal, it was found that HmBRI/D94N had a very high expression level (up to 40-70 mg/L culture) resulting in a dark purple cell pellet (FIG. 3A). The high-level expression, stability and visible purple pellet of HmBRI/D94N allowed the use of HmBRI/D94N as a tool for targeting integral membrane proteins to the membrane. Otherwise, wild-type HwBR has the highest expression level under our system, and studies of its functions and the properties as a fusion tag are ongoing.

Construction of the BR Fusion System with Different Target Membrane Proteins

The strategy for the construction of the BR fusion system is shown in FIG. 2B. The target gene, *E. coli* uppP, was constructed in pET28a with a 6×His tag, a thrombin cleavage site and a T7 tag at the 5' end. Because HmBRI/D94N can be expressed well in pET21b with C-terminal 6×His tag, we designed primers with specific restriction enzyme sites and subcloned the thrombin cleavage site-T7 tag-uppP fragment, constructed from pET28a, into the 3' end of Hmbop1/D94N. First, we introduced a Factor Xa cleavage site (IEGR↓) between Hmbop1/D94N and the His tag. Elongation of a 6×His into a 12×His tag can enhance the binding affinity of the fusion protein on a Ni-NTA column. TEV protease (TEVp) is a commonly used protease with high specificity for cleaving the affinity tag from the target proteins (Kapust et. al. (2001.) *Protein Eng* 14: 993-1000). Here, we substituted the thrombin cleavage site for a TEVp cleavage site (ENLYFQ↓G) to prepare the native target protein. If high-throughput screening of the target protein is required, the T7 tag (11 amino acids) generated from pET28a serves as a linker for the binding space of TEVp. The length of the linker can be adjusted depending on the characteristics of each protein.

Figure 8A:
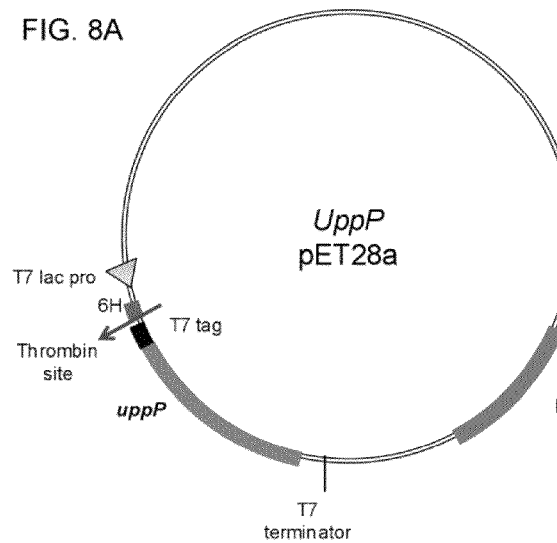
FIG. 8 shows vector maps of: (A) uppP cloned in pET28a; (B) Hmbop1/D94N cloned in pET21b; and (C) Hmbop1/D94N-uppP cloned in pET21b.
Figure 8B:
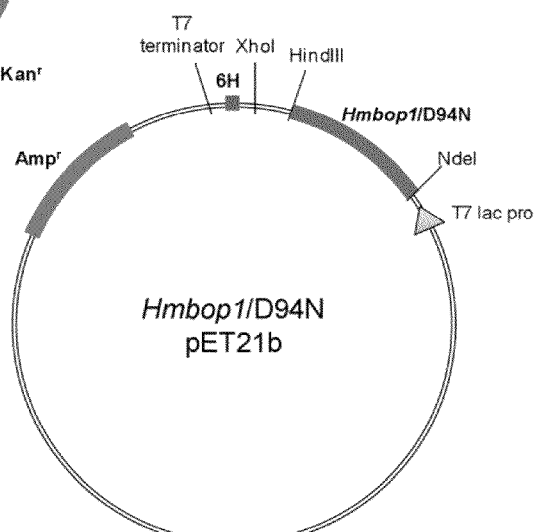
Figure 8C:
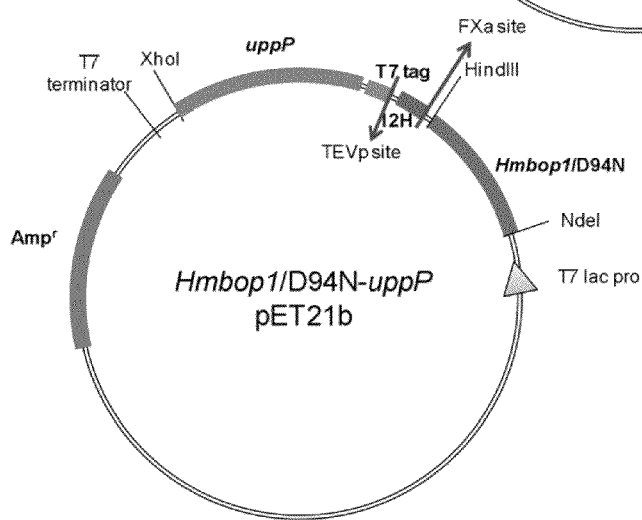

FIG. 8A shows a vector map of uppP cloned in pET28a. The *E. coli* uppP gene was constructed in the multiple cloning site of pET28a. The 5' end of uppP is 6 His tag followed by a thrombin cleavage site and T7 tag. FIG. 8B shows a vector map of Hmbop1/D94N cloned in pET21b. The *H. marismortui* bop1 gene was constructed in the multiple cloning site of pET21b between NdeI and HindIII. The resulted protein was followed by a 6 His tag at C terminus for purification. FIG. 8C shows a vector map of Hmbop1/D94N-uppP cloned in pET21b. The Hmbop1/D94N-uppP gene was cloned as a fusion protein. The vector was modified as a Hmbop1/D94N fusion tag followed by a 12-His-tag, a Fxa cleavage site, a T7 tag as a longker and a TEVp cleavage site. The target gene (e.g., uppP) was constructed between BamHI and XhoI with a stop codon.

To increase the purity of CaiT, a Strep purification tag was inserted at the C terminus of CaiT for further purification.

Expression and Purification of the Proteins

To avoid the toxicity associated with the over-expression of heterologous membrane proteins in *E. coli*, we used mutant *E. coli* strains, C41(DE3) and C43(DE3), which are routinely used as host cells for successful expression BR membrane protein (Miroux et al. (1996) *J Mol Biol* 260: 289-298). In our strategy, we established the same expression and purification steps for all of the constructs in order to consistently compare the expression level of each sample; however, the expression conditions for each construct could be tailored specifically designed to obtain the maximal expression yield.

All of the proteins in this research were expressed according to the same general protocol. When the cell density of each culture reached an $OD_{600}$ of 1.0, protein expression was induced with 0.5 mM isopropyl-β-D-thiogalactoside (IPTG) for 5 h at 37° C. in the presence of 5-10 μM all-trans retinal. HmBRI and mutant D94N were cloned into pET21b with a C-terminal 6×His tag and expressed in *E. coli* C43(DE3). The expressed *E. coli* cell pellets can be easily detected visually (FIG. 3A). pET21b, HmBRI and D94N expressed in *E. coli* C43(DE3) adding all-trans retinal resulted in white, purple and dark purple cell pellets.

To purify HmBRI/D94N, we treated the cell lysate in 50° C. water bath for 30 mins, based on the heat stable property of BR after cell disruption (Yokoyama et al. (2002) *J Biochem* 131: 785-790). The pellet containing the membrane fraction was extracted with n-decyl-β-D-maltoside (2%, DM) followed by Ni-NTA column purification, and HmBRI/D94N was eluted with 500 mM imidazole. We obtained approximately 70 mg/L culture of purified HmBRI/D94N for crystallization.

Detergents are critical components for extracting membrane proteins. To search for the proper detergents in purification of HmBRI/D94N and to improve the wide-range usage of the fusion tag system, several common detergents were used to extract the HmBRI/D94N protein. DM, UDM (n-undecyl-β-D-Maltoside), DDM (n-dodecyl-β-D-maltoside), OG (n-octyl-β-D-glucoside), NG (n-nonyl-β-D-glucoside) and LDAO (lauryldimethylamine-N-oxide) have different critical micelle concentrations (CMCs) and chemical and physical characteristics and were used to test the solubility of active HmBRI/D94N. The yields of detergent solubilization could be estimated by $A_{280}$ (total proteins) and $A_{552}$ (functional HmBRI/D94N) in the detergent-solubilized membranes (FIG. 3B). The results show that these six detergents could solubilize an equal amount of proteins in the membrane fraction. The active HmBRI/D94N protein could be solubilized by most detergents except LDAO. The use of LDAO might have caused the HmBRI/D94N to fold like opsin, without bound retinal, which might be quenched by LDAO. DM, UDM, DDM, OG and NG were able to be used in suitable buffer conditions for extracting the HmBRI/D94N fusion proteins for subsequent purification of the active target proteins.

Characterization of BRs

Figure 4:
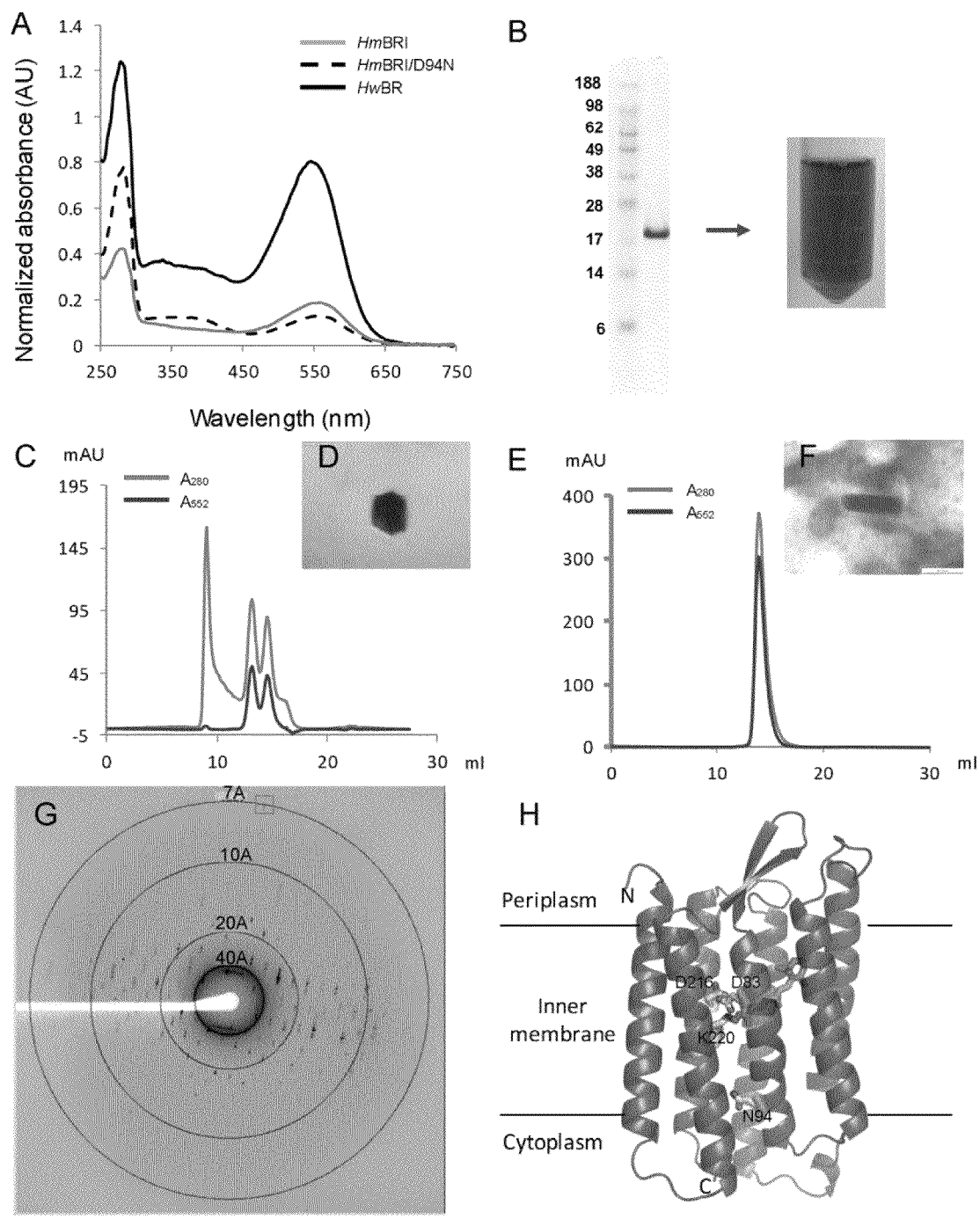
FIG. 4 shows the results of characterization of BRs. (A) The absorbance spectrum of BRs. The UV-Vis scan was plotted from 250 to 750 nm, and the absorbance peak is at 552 nm. (B) The purified HmBRI/D94N, which shows a single band on SDS-PAGE, is a purple solution. The SEC profile (C) and crystal (D) of purified HmBRI/D94N and the SEC profile (E) and crystal (F) of HwBR are shown. (G) The X-ray diffraction pattern and (H) the structural modeling of HmBRI/D94N.

The UV-VIS spectra scanning of purified HmBRI, D94N and HwBR qualitatively showed that these BRs are functional, as revealed by their specific absorption peak at 552 nm (FIG. 4A). Large-scale expression and purification of HmBRI/D94N showed a single band by SDS-PAGE (FIG. 4B). To obtain high-quality proteins, achieving a single elution peak monodispersed from a size exclusion column (SEC) is essential for membrane protein structural determination. The SEC result of purified HmBRI/D94N showed that some aggregated opsin (rhodopsin without retinal) in the void volume, and two conformations of this protein equilibrated simultaneously (FIG. 4C). The robotic screened crystallization conditions of purified HmBRI/D94N in 50 mM MES, pH 6.5, 150 mM NaCl, and 0.2% DM using vapor diffusion method were found in several commercial kits for membrane proteins (Molecular Dimensions, Inc.). The hexagonal purple crystals (FIG. 4D) grown in 50 mM sodium acetate, pH 4.2, 30% PEG 600 and 0.2 M calcium chloride showed the best X-ray diffraction, up to 7 Å resolution, using BL44XU at Spring-8 (FIG. 4G). Even though we could not obtain the HmBRI/D94N structure due to low-resolution data and detergent packing in the crystal (strong diffraction at approximately 40 Å), a homologous model using HsBR (1C3W) as the template was obtained (FIG. 4H). The N terminus of HmBRI/D94N is located in the periplasma, while the C terminus is located in cytoplasm. The K220 residue bound with retinal through a Schiff base interaction, and the key residues charged protonation, D83, D216 and the N94 mutant are located in the center channel of the protein. Interestingly, the purified HwBR presented a monodispersed peak in 50 mM sodium acetate, pH 4.5, 150 mM NaCl, and 0.2% DM after a series of buffer and detergent screens (FIG. 4E). Using crystallization screening kits, the hexagonal purple crystals (FIG. 4F) grown in 0.2 M calcium chloride, 0.1 M Tris-HCl, pH 8.0, 44% PEG 400 showed X-ray diffraction pattern to 10 Å resolution (data collected using in-house Rigaku FR-E X-ray generator).

Characterization of the Target Integral Membrane Proteins UppP and CaiT

Figure 5A:
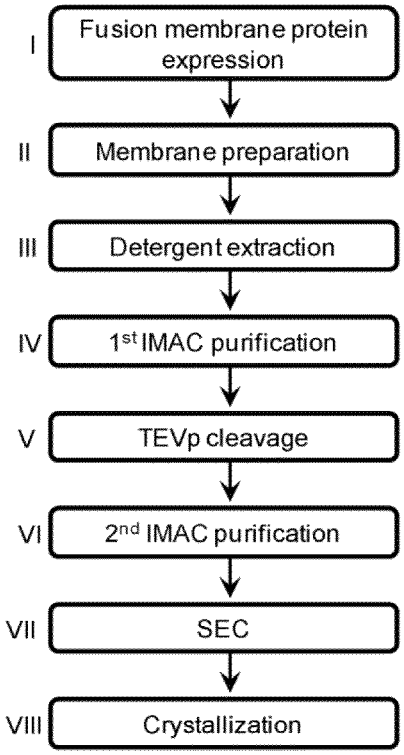
FIG. 5 shows fusion protein expression. (A) A flow chart illustrating the purification strategy for the HmBRI/D94N fusion membrane protein. Step I: *E. coli* C43 or C41(DE3) expression. Step II: Collection of the purple membrane fraction by ultracentrifugation. Step III: Detergent extraction of the purple membrane. Step IV: Application of the purple protein solution to the $1^{st}$ Immobilized metal ion affinity chromatography (IMAC) column and collection of the eluted fusion protein. Step V: TEV protease digestion of the fusion protein. Step VI: Reverse IMAC column purification, with the target protein collected in the flow-through. Step VII: Size exclusion column (SEC) chromatography, resulting in a monodispersed peak. Step VIII: Crystallization. (B) Topology prediction for the HmBRI/D94N-UppP fusion protein. (C) Expression cell pellets of HmBRI/D94N (DN). DN-UppP and DN-CaiT. (D) Expression level of UppP (dark purple bar) and CaiT (light purple bar). 1. Gene constructed in pET51. 2. Protein purified from DN fusion system. 3. Protein expression in literature. $^a$Data from Ghachi et al. (2004) (J Biol Chem 279: 30106-30113). $^b$Data from Vinothkumar et al. (2006) (J Biol Chem 281: 4795-4801).
Figure 5B:
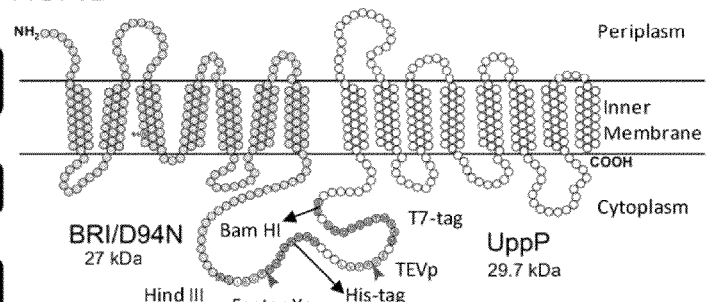

Most membrane proteins function as channels, receptors, transporters and signal transduction elements. To examine whether the target protein obtained in our HmBRI/D94N fusion tag system adopts the correct fold, we selected the integral membrane enzymes undecaprenyl pyrophosphate phosphatase (UppP), and carnitine/butyrobetaine antiporter (CaiT), as they both could be assayed, as the target membrane proteins. Based on our cloning strategy, a flowchart for the purification of each target protein using the fusion purification system was established (FIG. 5A). To enhance the binding affinity of the fusion protein, we introduced a 12×His tag. The fusion protein was eluted using 500 mM imidazole during the first IMAC column purification step. In the fusion protein, downstream from the His tag for affinity column binding, we introduced a TEVp cleavage site at the N-terminus of the target protein to obtain the native form by proteolytic digestion. After cleavage with TEVp, a second IMAC column was used to remove the uncleaved fusion protein and the His tagged TEVp and HmBRI/D94N. The target protein was collected in the flow-through fractions. Since SEC was commonly used in membrane protein purification for obtaining homogeneous membrane protein. SUPERDEX™ 200 HR 10/30 column was used for the final step of purification. The topology diagram predicted for the fusion membrane protein-HmBRI/D94N-UppP, which facilitated the visualization of the purification steps, is shown in FIG. 5B.

Figure 5C:
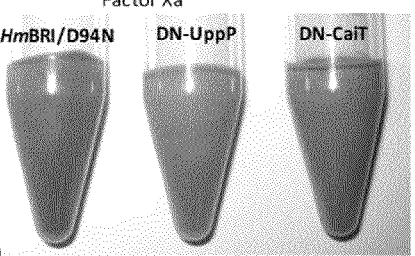
Figure 5D:
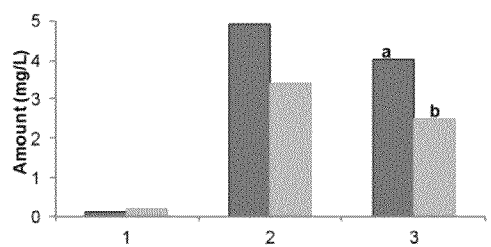

The expression pellets for the HmBRI/D94N, -UppP and -CaiT fusions all appeared purple in color (FIG. 5C). Compared to the expression levels when using pET51 expression vector without a fusion tag (0.1 and 0.2 mg/L), expression of UppP and CaiT using the fusion system enhanced the overall expression level by 50- and 17-fold (4.9 and 3.4 mg/L), respectively. The amounts of purified UppP and CaiT were still greater than the amounts reported in previous studies (4 and 2.5 mg/L) (Ghachi et al. (2004) *J Biol Chem* 279: 30106-30113; Vinothkumar et al. (2006) *J Biol Chem* 281: 4795-4801) (FIG. 5D).

Figure 6A:
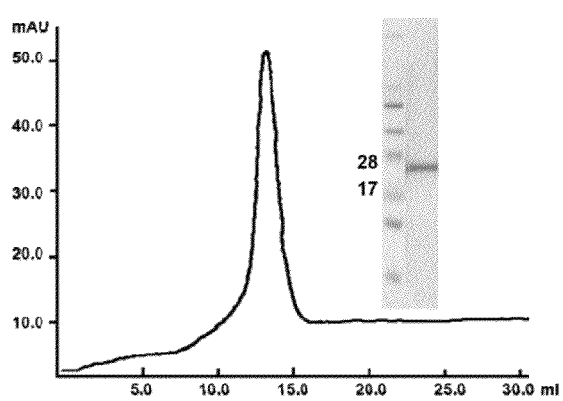
FIG. 6 shows the results of purification and functional assay of UppP. (A) The monodispersed peak fraction at the final step of UppP purification showed a single hand on the SDS-PAGE. (B) The time dependence of UppP phosphatase activity was presented using Fpp as the substrate.
Figure 6B:
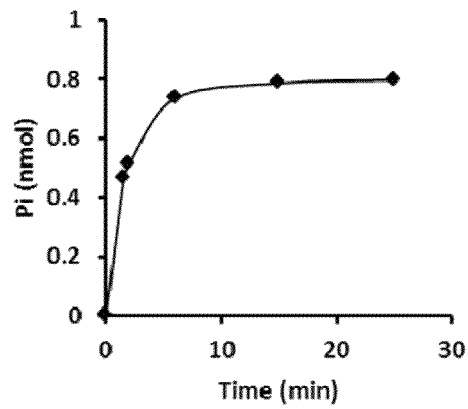

The purified UppP showed a monodispersed peak by SEC and a single band by SDS-PAGE (FIG. 6A). For testing the phosphatase activity of UppP, assays were performed in the presence of various substrates using Malachite Green assay. Since the intended substrate, Upp, was difficult to synthesize and purify (Ghachi et al. Id.), we used farnesyl pyrophosphate (Fpp) as a model substrate. It was previously reported that another *E. coli* undecaprenyl pyrophosphate phosphatase, PgpB, which has no sequence homology with UppP, catalyzed the dephosphorylation of Upp with a relatively low efficiency compared to diacylglycerol pyrophosphate and farnesyl pyrophosphate lipid substrates. In our activity assay test, Fpp was a suitable substrate for UppP. A time-dependent phosphatase assay showed that purified UppP was a functional protein capable of releasing free phosphate (FIG. 6B).

Figure 7:
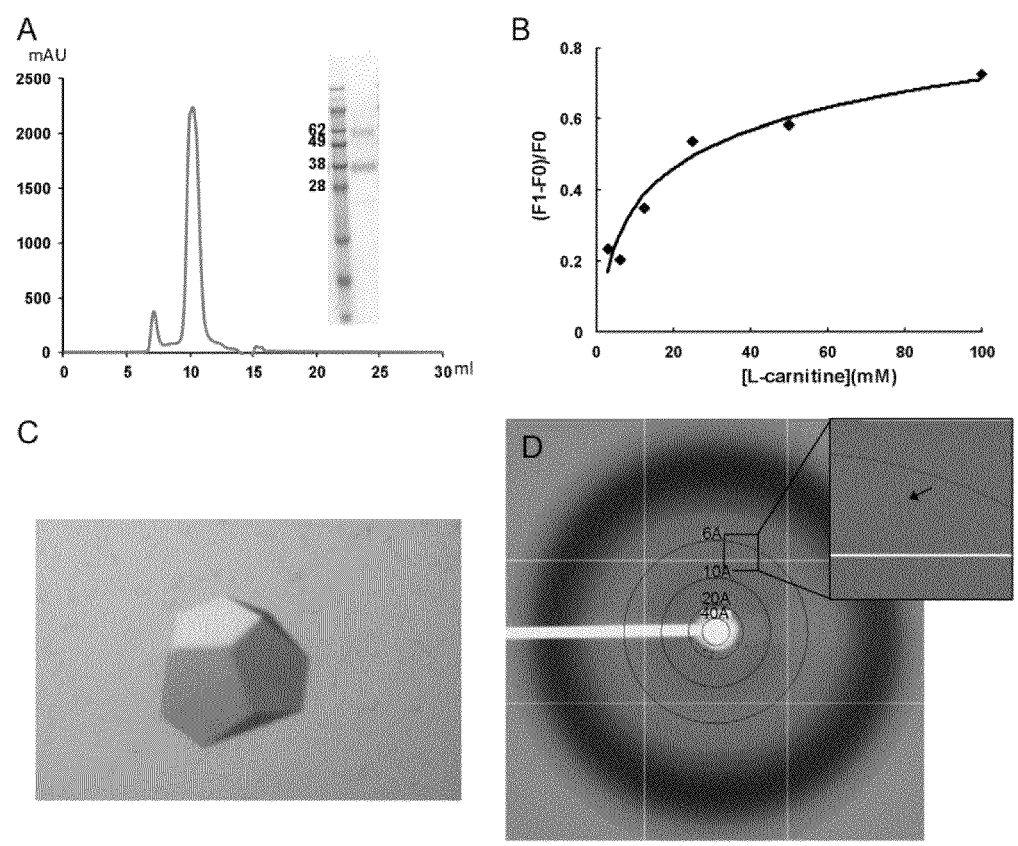
FIG. 7 shows the results of characterization of CaiT. (A) Size exclusion column of CaiT purification. (B) Binding of L-carnitine in CaiT. (C) Crystal of CaiT. (D) X-ray diffraction of the crystal with resolution up to 6.5 Å where the arrow shows.

The purified CaiT showed a monodispersed SEC peak (FIG. 7A). The binding affinity of L-carnitine in CaiT was shown in FIG. 7B. We grew crystals of the functional CaiT (FIG. 7C), and the best spot of x-ray diffraction was up to 6.5 Å (FIG. 7D) and the diffraction data are shown in Table 1.

TABLE 1

Data collection statistics

| Sample name | HmBRI/D94N | CaiT |
|---|---|---|
| Beamline | 44XU, Spring8 | 13B1, NSRRC |
| Wavelength (Å) | 1.5 | 1 |
| Space group | P622 | $P3_2$ |
| Cell dimensions | | |
| a, b, c (Å) | 185, 185, 585 | 131, 131, 156 |
| γ (°) | 120 | 120 |
| Resolution (Å) | 34.0-8.7 (8.85-8.70) | 30.0-7.0 (7.25-7.00) |
| $R_{merge}$ | 0.10 (0.58) | 0.045 (0.64) |
| I/σI | 34.0 (7.3) | 41.8 (2.8) |
| Completeness (%) | 96.0 (97.7) | 99.9 (100.0) |
| Redundancy | 11.3 (12.0) | 7.1 (6.9) |

Based on homology modeling study, HmBRI has seven transmembrane α helices and two β strands conformation bound to the chromophore retinal. Several rhodopsins from various halobacteria have been expressed with a His-tag in *E. coli*, producing unstable, inclusion body or low-yield heterologous expression of rhodopsins (Braiman et al (1987) *J Biol Chem* 262: 9271-9276; Dunn et al. (1987) *J. Biol Chem* 262: 9246-9254; Schmies et al. (2000) FEBS Lett 466: 67-69). The invention is related to the discovery that HmBRI/D94N had the highest expression yield (~70 mg/L) when using the most common pET expression system in *E. coli* under modified expression conditions. The macroscopic HmBRI/D94N appearance was useful for quick measurements of protein expression levels because it could be measured quantitatively by UV/VIS absorption. In our purple BR-fusion membrane protein expression system, the N terminus of the target membrane protein is located in the cytoplasm as the HmBRI/D94N is a GPCR, which normally has its C terminus at the cytoplasmic site. To test the novel macroscopic HmBRI/D94N fusion tag system, UppP and CaiT were used as examples to demonstrate that our strategy indeed could produce functional proteins. Furthermore, HwBR was expressed at high levels and purified with a monodispersed peak on an SEC column. Monodispersity is very important for membrane protein crystallization. A fusion tag that is able to produce a monodispersed peak can be used to assess suitable detergents and help crystal packing, similar to other systems, such as GFP and T4 lysozyme. Our results suggested that HwBR might be the next-generation BR-fusion membrane protein expression tag.

In conclusion, we have designed an effective platform with several advantages for preparing integral membrane proteins. HmBRI/D94N and HwBR can target proteins of interest to the membrane and facilitate these membrane proteins to fold properly. Because correctly folded photoreceptors form purple membrane, we can directly visualize the expressed proteins and estimate the expression level of the fusion proteins. The expression level of the target membrane proteins may be increased, stimulated by the high expression level of HmBRI/D94N or HwBR. Separation of the fusion tag and the target protein can be efficiently achieved by protease digestion, yielding the target membrane protein. Using HmBRI/D94N or HwBR as a novel membrane protein expression tag will allow researchers to express and produce native membrane proteins.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. An expression vector comprising:
   a) a polynucleotide sequence encoding a mutant bacteriorhodopsin having at least 80% sequence identity to SEQ ID NO: 1;
   b) a multiple cloning site, located downstream from the polynucleotide encoding the mutant bacteriorhodopsin;
   c) a T7 promoter, operably linked to the polynucleotide sequence encoding the mutant bacteriorhodopsin,
   d) a nucleic acid sequence encoding a polyhistidine tag, located downstream from the polynucleotide sequence encoding the mutant bacteriorhodopsin and upstream from the multiple cloning site;
   e) a first polynucleic acid encoding a first protease cleavage site, located downstream from the nucleic acid sequence encoding the polyhistidine tag and upstream from the multiple cloning site;
   f) optionally a second polynucleic acid encoding a second protease cleavage site, located between the polynucleotide sequence encoding the mutant bacteriorhodopsin and the nucleic acid sequence encoding the polyhistidine tag; and
   g) optionally a nucleotide sequence encoding a linker located between the first polynucleic acid encoding the first protease cleavage site and the multiple cloning site;
   wherein the mutant bacteriorhodopsin retains Asn94 of SEQ ID NO: 1.

2. The expression vector of claim 1, wherein the polynucleotide encodes a mutant bacteriorhodopsin having at least 90% sequence identity to SEQ ID NO: 1.

3. The expression vector of claim 2, wherein the polynucleotide encodes a mutant bacteriorhodopsin having the amino acid sequence of SEQ ID NO: 1.

4. The expression vector of claim 3, further comprising a DNA encoding a target membrane protein, the DNA encoding the target membrane protein being located within the multiple cloning site.

5. The expression vector of claim 1, wherein the polyhistidine tag contains more than 6 histidine residues.

6. The expression vector of claim 1, wherein the first protease cleavage site is a Tobacco Etch Virus protease cleavage site and the second protease cleavage site is a factor Xa cleavage site.

7. The expression vector of claim 1, further comprising a DNA encoding a target membrane protein the DNA encoding the target membrane protein being located within the multiple cloning site.

8. A host cell comprising the expression vector of claim 7.

9. The host cell of claim 8, which expresses a fusion protein comprising the mutant bacteriorhodopsin and the target membrane protein, wherein the N-terminus of the target membrane protein is located in the cytoplasm, and the host cell exhibits a purple color.

10. The expression vector of claim 1, wherein the expression vector comprises the nucleotide sequence encoding the linker, wherein the linker is a T7 tag.

* * * * *

SEQUENCE LISTING

```
<160> NUMBER OF SEQ ID NOS: 5

<210> SEQ ID NO 1
<211> LENGTH: 250
<212> TYPE: PRT
<213> ORGANISM: Haloarcula marismortui

<400> SEQUENCE: 1

Met Pro Ala Pro Gly Ser Glu Gly Ile Trp Leu Trp Leu Gly Thr Ala
1               5                   10                  15

Gly Met Phe Leu Gly Met Leu Tyr Phe Ile Ala Arg Gly Trp Gly Glu
            20                  25                  30

Thr Asp Gly Arg Arg Gln Lys Phe Tyr Ile Ala Thr Ile Leu Ile Thr
        35                  40                  45
```

```
Ala Ile Ala Phe Val Asn Tyr Leu Ala Met Leu Gly Phe Gly Leu
    50                  55                  60

Thr Phe Ile Glu Phe Gly Glu Gln His Pro Ile Tyr Trp Ala Arg
65                  70                  75                  80

Tyr Thr Asp Trp Leu Phe Thr Thr Pro Leu Leu Tyr Asn Leu Gly
                    85                  90                  95

Leu Leu Ala Gly Ala Asp Arg Asn Thr Ile Tyr Ser Leu Val Ser Leu
                100                 105                 110

Asp Val Leu Met Ile Gly Thr Gly Val Val Ala Thr Leu Ser Ala Gly
            115                 120                 125

Ser Gly Val Leu Ser Ala Gly Ala Glu Arg Leu Val Trp Trp Gly Ile
130                 135                 140

Ser Thr Ala Phe Leu Leu Val Leu Leu Tyr Phe Leu Phe Ser Ser Leu
145                 150                 155                 160

Ser Gly Arg Val Ala Asn Leu Pro Ser Asp Thr Arg Ser Thr Phe Lys
                165                 170                 175

Thr Leu Arg Asn Leu Val Thr Val Val Trp Leu Val Tyr Pro Val Trp
                180                 185                 190

Trp Leu Val Gly Ser Glu Gly Leu Gly Leu Val Gly Ile Gly Ile Glu
                195                 200                 205

Thr Ala Gly Phe Met Val Ile Asp Leu Val Ala Lys Val Gly Phe Gly
210                 215                 220

Ile Ile Leu Leu Arg Ser His Gly Val Leu Asp Gly Ala Ala Glu Thr
225                 230                 235                 240

Thr Gly Thr Gly Ala Thr Pro Ala Asp Asp
                245                 250

<210> SEQ ID NO 2
<211> LENGTH: 250
<212> TYPE: PRT
<213> ORGANISM: Haloarcula marismortui

<400> SEQUENCE: 2

Met Leu Pro Leu Gln Val Ser Ser Leu Gly Val Glu Gly Gly Gly Ile
1               5                   10                  15

Trp Leu Ala Leu Gly Thr Val Gly Met Leu Leu Gly Met Val Tyr Phe
                20                  25                  30

Met Ala Lys Gly Trp Asp Val Gln Asp Pro Glu Gln Glu Glu Phe Tyr
            35                  40                  45

Val Ile Thr Ile Leu Ile Ala Gly Ile Ala Ala Ser Ser Tyr Leu Ser
    50                  55                  60

Met Phe Phe Gly Phe Gly Leu Thr Glu Val Glu Leu Val Asn Gly Arg
65                  70                  75                  80

Val Ile Asp Val Tyr Trp Ala Arg Tyr Ala Asp Trp Leu Phe Thr Thr
                    85                  90                  95

Pro Leu Leu Leu Leu Asp Ile Gly Leu Leu Ala Gly Ala Ser Asn Arg
                100                 105                 110

Asp Met Ala Ser Leu Ile Thr Ile Asp Ala Phe Met Ile Val Thr Gly
            115                 120                 125

Leu Ala Ala Thr Leu Met Lys Val Pro Val Ala Arg Tyr Ala Phe Trp
130                 135                 140

Thr Ile Ser Thr Ile Ala Met Leu Phe Val Leu Tyr Tyr Leu Val Val
145                 150                 155                 160
```

```
Val Val Gly Glu Ala Ala Ser Asp Ala Ser Glu Glu Ala Gln Ser Thr
            165                 170                 175

Phe Asn Val Leu Arg Asn Ile Ile Leu Val Ala Trp Ala Ile Tyr Pro
        180                 185                 190

Val Ala Trp Leu Val Gly Thr Glu Gly Leu Gly Leu Val Gly Leu Phe
            195                 200                 205

Gly Glu Thr Leu Leu Phe Met Ile Leu Asp Leu Thr Ala Lys Ile Gly
        210                 215                 220

Phe Gly Phe Ile Leu Leu Arg Ser Arg Ala Ile Val Gly Gly Asp Ser
225                 230                 235                 240

Ala Pro Thr Pro Ser Ala Glu Ala Ala Asp
            245                 250

<210> SEQ ID NO 3
<211> LENGTH: 254
<212> TYPE: PRT
<213> ORGANISM: haloquadratum walsbyi

<400> SEQUENCE: 3

Met Ser Gln Leu Ala Leu Gln Met Ser Ser Leu Gly Val Glu Gly Glu
1               5                   10                  15

Gly Ile Trp Leu Ala Leu Gly Thr Ile Gly Met Leu Gly Met Leu
            20                  25                  30

Tyr Phe Ile Ala Asp Gly Leu Asp Val Gln Asp Pro Arg Gln Lys Glu
        35                  40                  45

Phe Tyr Val Ile Thr Ile Leu Ile Pro Ala Ile Ala Ala Ala Ser Tyr
    50                  55                  60

Leu Ser Met Phe Phe Gly Phe Gly Leu Thr Glu Val Ser Leu Ala Asn
65                  70                  75                  80

Gly Arg Val Val Asp Val Tyr Trp Ala Arg Tyr Ala Asp Trp Leu Phe
                85                  90                  95

Thr Thr Pro Leu Leu Leu Leu Asp Ile Gly Leu Leu Ala Gly Ala Ser
            100                 105                 110

Gln Arg Asp Ile Gly Ala Leu Val Gly Ile Asp Ala Phe Met Ile Val
        115                 120                 125

Thr Gly Leu Val Ala Thr Leu Thr Lys Val Val Ala Arg Tyr Ala
    130                 135                 140

Phe Trp Thr Ile Ser Thr Ile Ser Met Val Phe Leu Leu Tyr Tyr Leu
145                 150                 155                 160

Val Ala Val Phe Gly Glu Ala Val Ser Asp Ala Asp Glu Asp Thr Arg
                165                 170                 175

Ser Thr Phe Asn Ala Leu Arg Asn Ile Ile Leu Val Thr Trp Ala Ile
            180                 185                 190

Tyr Pro Val Ala Trp Leu Val Gly Thr Glu Gly Leu Ala Leu Thr Gly
        195                 200                 205

Leu Tyr Gly Glu Thr Leu Leu Phe Met Val Leu Asp Leu Val Ala Lys
    210                 215                 220

Val Gly Phe Gly Phe Ile Leu Leu Arg Ser Arg Ala Ile Met Gly Gly
225                 230                 235                 240

Gly Ser Glu Pro Thr Pro Ser Ala Gln Glu Thr Ala Ala Asp
                245                 250

<210> SEQ ID NO 4
<211> LENGTH: 248
<212> TYPE: PRT
<213> ORGANISM: Halobacterium salinarum
```

```
<400> SEQUENCE: 4

Gln Ala Gln Ile Thr Gly Arg Pro Glu Trp Ile Trp Leu Ala Leu Gly
1               5                   10                  15

Thr Ala Leu Met Gly Leu Gly Thr Leu Tyr Phe Leu Val Lys Gly Met
            20                  25                  30

Gly Val Ser Asp Pro Asp Ala Lys Lys Phe Tyr Ala Ile Thr Thr Leu
        35                  40                  45

Val Pro Ala Ile Ala Phe Thr Met Tyr Leu Ser Met Leu Leu Gly Tyr
    50                  55                  60

Gly Leu Thr Met Val Pro Phe Gly Gly Glu Gln Asn Pro Ile Tyr Trp
65              70                  75                      80

Ala Arg Tyr Ala Asp Trp Leu Phe Thr Thr Pro Leu Leu Leu Leu Asp
                85                  90                  95

Leu Ala Leu Leu Val Asp Ala Asp Gln Gly Thr Ile Leu Ala Leu Val
            100                 105                 110

Gly Ala Asp Gly Ile Met Ile Gly Thr Gly Leu Val Gly Ala Leu Thr
        115                 120                 125

Lys Val Tyr Ser Tyr Arg Phe Val Trp Trp Ala Ile Ser Thr Ala Ala
    130                 135                 140

Met Leu Tyr Ile Leu Tyr Val Leu Phe Phe Gly Phe Thr Ser Lys Ala
145                 150                 155                 160

Glu Ser Met Arg Pro Glu Val Ala Ser Thr Phe Lys Val Leu Arg Asn
                165                 170                 175

Val Thr Val Val Leu Trp Ser Ala Tyr Pro Val Val Trp Leu Ile Gly
            180                 185                 190

Ser Glu Gly Ala Gly Ile Val Pro Leu Asn Ile Glu Thr Leu Leu Phe
        195                 200                 205

Met Val Leu Asp Val Ser Ala Lys Val Gly Phe Gly Leu Ile Leu Leu
    210                 215                 220

Arg Ser Arg Ala Ile Phe Gly Glu Ala Glu Ala Pro Glu Pro Ser Ala
225                 230                 235                 240

Gly Asp Gly Ala Ala Ala Thr Ser
                245

<210> SEQ ID NO 5
<211> LENGTH: 250
<212> TYPE: PRT
<213> ORGANISM: Haloarcula marismortui

<400> SEQUENCE: 5

Met Pro Ala Pro Gly Ser Glu Gly Ile Trp Leu Trp Leu Gly Thr Ala
1               5                   10                  15

Gly Met Phe Leu Gly Met Leu Tyr Phe Ile Ala Arg Gly Trp Gly Glu
            20                  25                  30

Thr Asp Gly Arg Arg Gln Lys Phe Tyr Ile Ala Thr Ile Leu Ile Thr
        35                  40                  45

Ala Ile Ala Phe Val Asn Tyr Leu Ala Met Ala Leu Gly Phe Gly Leu
    50                  55                  60

Thr Phe Ile Glu Phe Gly Gly Glu Gln His Pro Ile Tyr Trp Ala Arg
65              70                  75                      80

Tyr Thr Asp Trp Leu Phe Thr Thr Pro Leu Leu Leu Tyr Asp Leu Gly
                85                  90                  95

Leu Leu Ala Gly Ala Asp Arg Asn Thr Ile Tyr Ser Leu Val Ser Leu
            100                 105                 110
```

```
Asp Val Leu Met Ile Gly Thr Gly Val Val Ala Thr Leu Ser Ala Gly
        115                 120                 125

Ser Gly Val Leu Ser Ala Gly Ala Glu Arg Leu Val Trp Trp Gly Ile
        130                 135                 140

Ser Thr Ala Phe Leu Leu Val Leu Leu Tyr Phe Leu Phe Ser Ser Leu
145                 150                 155                 160

Ser Gly Arg Val Ala Asn Leu Pro Ser Asp Thr Arg Ser Thr Phe Lys
                165                 170                 175

Thr Leu Arg Asn Leu Val Thr Val Val Trp Leu Val Tyr Pro Val Trp
                180                 185                 190

Trp Leu Val Gly Ser Glu Gly Leu Gly Leu Val Gly Ile Gly Ile Glu
        195                 200                 205

Thr Ala Gly Phe Met Val Ile Asp Leu Val Ala Lys Val Gly Phe Gly
        210                 215                 220

Ile Ile Leu Leu Arg Ser His Gly Val Leu Asp Gly Ala Ala Glu Thr
225                 230                 235                 240

Thr Gly Thr Gly Ala Thr Pro Ala Asp Asp
                245                 250
```